(12) United States Patent
Landtved et al.

(10) Patent No.: US 11,330,801 B2
(45) Date of Patent: May 17, 2022

(54) URINE COLLECTION DEVICE FOR ANIMALS

(71) Applicant: PEE WIZZ IP HOLDING LLC., Delray Beach, FL (US)

(72) Inventors: Bende Søndergaard Landtved, Otterup (DK); Johan Skjellerup, Delray Beach, FL (US)

(73) Assignee: PEE WIZZ IP HOLDING LLC., Delray Beach, FL (US)

( * ) Notice: Subject to any disclaimer, the term of this patent is extended or adjusted under 35 U.S.C. 154(b) by 120 days.

(21) Appl. No.: 16/992,830

(22) Filed: Aug. 13, 2020

(65) Prior Publication Data

US 2022/0046898 A1    Feb. 17, 2022

(51) Int. Cl.
*A01K 23/00*      (2006.01)

(52) U.S. Cl.
CPC ................... *A01K 23/00* (2013.01)

(58) Field of Classification Search
CPC ........ A01K 23/00; A01K 1/01; A01K 27/002; A01K 27/008; A01K 23/005
USPC ................. 119/868, 869; 604/317
See application file for complete search history.

(56) References Cited

U.S. PATENT DOCUMENTS

| | | | | |
|---|---|---|---|---|
| 3,656,459 A | * | 4/1972 | Missud | A01K 23/00 119/868 |
| 4,502,417 A | * | 3/1985 | Jenkins | A01K 23/00 119/868 |
| 5,819,691 A | * | 10/1998 | Lavi | A01K 23/00 119/868 |
| 5,937,795 A | * | 8/1999 | Raphael | A01K 23/00 119/869 |
| 10,582,699 B1 | * | 3/2020 | Arthurs | A01K 23/00 |
| 2002/0091363 A1 | * | 7/2002 | Vella | A01K 23/00 604/323 |
| 2018/0206453 A1 | * | 7/2018 | Stoccardo | A01K 23/00 |
| 2019/0116761 A1 | * | 4/2019 | Walter | A01K 23/00 |
| 2019/0343082 A1 | * | 11/2019 | Yeboah, Jr. | A01K 27/008 |

* cited by examiner

*Primary Examiner* — Yvonne R Abbott-Lewis
(74) *Attorney, Agent, or Firm* — Malloy & Malloy, PL (57) ABSTRACT

A device for collecting urine from a mammal including a base removably disposed in an operative position overlying at least an under portion of the mammal. An access opening is formed in the base in urine receiving relation to the mammal, when in the operative position. A receptacle, is removably connected to said base, in the urine receiving relation to the mammal, via said access opening and a closure, integrated in said receptacle, is disposable between an open orientation and a closed orientation, for receiving and retaining collected urine within an interior of the receptacle. The base may also include a retaining aperture disposed and structured to receive and retain a tale of the mammal therein, concurrent to said operative position.

20 Claims, 10 Drawing Sheets

URINE COLLECTION DEVICE FOR ANIMALS

BACKGROUND OF THE INVENTION

Field of the Invention

The present invention relates in general to the field of animal health, in particular to the health of mammals, such as cats and dogs. More specifically, the present invention relates to a device for collecting urine from the animal and an intended method of use of the collecting device.

Description of the Related Art

For many years it has been popular all over the world to keep animals as pets. A variety of animals are kept by people as pets in their homes. Some species of animals need, due to their wild nature, to be kept under captivity when used as pets, whereas other species of animals may live more freely, without having to live in a cage or be tethered. To the latter group belong cats, dogs and possibly other commonly domesticated animals appropriate to be kept as pets. Cats and dogs are rather long-lived animals, meaning that a person keeping a cat or a dog as a pet can have a life with that pet for many years. This fact may be one reason that a person keeping a cat or a dog as a pet find him-/herself to be strongly emotionally attached to that pet.

For obvious reasons, when a person is emotionally attached to a pet, that person cares for the health of the pet. Therefore, most people keeping a cat or a dog as a pet attend a veterinarian at regularly intervals in order to constantly monitor the state of health of the pet with the view to observe any possible complications at an early stage.

One way of monitoring the state of health of a pet, such as a cat or a dog, is to analyze the urine of the animal. By analyzing the urine of a pet, it will be possible to detect numerous different physiological dysfunctions of the pet. Additionally, during a period of medicating the animals, monitoring the content of the urine may help the veterinarian to assess the progressing of recovery of the pet. However, collecting urine from a cat, dog and possibly other domesticated animals which run around more or less freely, is not an easy task.

One may collect the urine from the cat's litter box or from the pavement or other ground surface, where a dog urinates using a pipette or other appropriate device. However, collecting urine this way is not at all a sterile way of collection and once having been in contact with the cat litter, ground or other surface, the urine may be contaminated, thereby imparting components to the urine not originating from the pet.

Another way of collecting urine form a cat, dog or other pet may be for the owner to follow the pet and at a time where the pet makes preparation to urinate, such as by assuming a typical body position accompanying urination, the owner arranges a container or other collection device under the animal. Such collection devices may comprise an elongate handle capable of being held at one end thereof during the collection procedure. The other end includes a cup, retainer or appropriate receptable, which is intended for positioning, relative to the animal, while urinating. However many, if not most, cats and dogs are distracted or apprehensive when such a collection device is positioned below or in close proximity to their body during a time of urination, resulting in their movement and/or stopping of the urination procedure, in order to avoid the collection device.

In an attempt to overcome problems and disadvantages of the type set forth above, collection systems are known and/or have been developed. By way of example, devices exist for the purpose of collecting urine so that urine spills do not impart in-house damage. Such collection systems may be in the form of a diaper type structure formed as a pair of pants to be worn by a dog. As structured, the diaper comprises two holes, one for each leg. In addition collection system may also comprise a pad formed of an absorbent material which, when mounted, are located at the bottom side of the dog. The absorbent material is able to absorb urine and thereby avoid spreading of urine when the dog is moving around an indoor environment. However, diapers and other structures of this type do not facilitate the collection of urine for the purpose of using it in a medical and/or diagnostic procedure. Accordingly, while assumed to be operative for its intended purpose, additional disadvantages of this type may include very unhygienic procedural steps in order to release the urine from the absorbent material of the pad, such as manually squeezing the pad.

Other known devices disclose a urine collection may be intended for use on a male dog. As such, the device comprises a tube to be arranged around the penis of the dog. The tube is connected to a bag into which urine can flow, wherein the urine can be collected when the dog has finished urinating. More specifically, known prior art devices of this type include a urine collection device that hangs rather freely from the belly of the male dog, thereby representing the risk that the device will easily come off. Additionally, as the mounting of the tube of the device requires the careful step of arranging the tube around the penis of the dog, it may not be easily attached. Moreover, the male dog may not find it comfortable to have the tube arranged at the intended position. Finally, and for obvious reasons such a device is not suitable for use with female dogs.

Therefore, it is an objective of the present invention to provide an instrument, and attendant uses and methods which overcomes the problems and disadvantages of the type set forth above.

Specifically, it is an object of the present invention to provide a device for collecting urine from a mammal such as, but not necessarily limited to, a cat or a dog for the purpose of performing a diagnosis based on that urine.

It is a further object of the present invention to provide such a device which is quick and easy to secure on the mammal, while eliminating or significantly restricting discomfort to the mammal and where in the device is suitable for use on a mammal regardless of the sex of that animal.

SUMMARY OF THE INVENTION

The one or more embodiments of the present invention are directed to a device for collecting urine from an animal/mammal which comprises: a flexible sheet including a first surface operatively disposed in facing relation to the body of animal/mammal. The sheet also includes a second surface oppositely disposed to the first surface. Further, the flexible sheet includes an extension in a lengthwise direction and an extension in a transversal direction, the transversal direction being perpendicular to said lengthwise direction. The flexible sheet is at least partially made from a liquid and/or moisture impervious material.

When attached to the animal/mammal, the flexible sheet is disposed in an operative position and a specific location, wherein a first trough-going hole is formed in the flexible sheet and includes a predetermined or defining a circumference. In addition, a harness is attached to the flexible sheet and is disposed and structured to facilitate mounting at least part of said flexible sheet, in the operative position, below the pelvic region of the animal/mammal. One feature of the one or more preferred embodiments of the urine collecting device of the present invention is characterized by the inclusion of a receptable for collecting urine from the mammal. The receptacle comprises an inner surface and an outer surface, wherein the inner surface is separated from the outer surface by a rim portion. More specifically, the receptable is arranged in the first through-going hole at the rim portion thereof, so that the outer surface of said receptable extends away from said first through-going hole at the second surface of flexible sheet.

Additional aspects of the present invention relate to a use of a urine collecting device according to as described herein, wherein the preparation of performing a diagnostic analysis of mammal, based on the urine is facilitated.

In addition, the present invention provides a method for collecting urine from an animal/mammal, comprising:
i) providing a device according to the first aspect of the present invention;
ii) arranging device on the animal/mammal in such a way that the first surface of said flexible sheet is facing the mammal and in such a way that the receptacle is located below the pelvic region of the mammal;
iii) strapping the harness around a back and/or rear portion of the mammal in order to secure the device to the mammal;
iv) awaiting the animal to start urinating;
v) once urinating has finished, unstrapping the device from the mammal and securing the urine.

Yet another embodiment of the urine collection device of the present invention may be considered operationally similar, but at least partially distinguishable in structure. More specifically, this additional preferred embodiment includes a base which is correspondingly and cooperatively dimensioned and configured for at least partially covering relation to an animal/mammal on which it is mounted. As such, the base may include a flexible and possibly "stretchable" material sheet dimensioned and configuration to accommodate animals of different sizes and types.

In addition, a harness is connected to the base and serves to removably connect it in an operative position on the animal/mammal. The harness may include one or more straps or other appropriately structured members disposed in interconnecting relation to one another and/or to the base such that, when in the operative position, the base is disposed in overlying, covering relation to an under portion of the animal/mammal, such as generally beneath the pelvic area. Interconnection of the harness members may be accomplished by Velcro® or other removably connectable attachment members which facilitate the removable mounting of the base on the animal/mammal in the aforementioned operative position.

Additional features of this additional embodiment of the urine collection device of the present invention includes a receptacle having a hollow interior appropriately dimensioned to receive urine passed from the animal/mammal. Accordingly, the receptacle is connected to the base in urine receiving relation to the mammal, concurrent to the base being mounted on the animal in the aforementioned operative position. Further, the receptacle preferably includes a closure structured for disposition in a closed orientation and an open orientation relative to the hollow interior thereof. The closure is cooperatively structured with the base and its attachment thereto such that the closure may be selectively disposed in either of the closed or open orientations concurrent to the being connected to the base, while the base is disposed in the operative position on the animal/mammal. Additional structural features of the closure facilitate it defining a substantially fluid tight seal, when in the closed orientation thereby preventing or significantly restricting leakage of the collected urine from the interior of the receptacle.

This additional preferred embodiment of the urine collection device also includes a connecting structure attached to the receptacle and structured to removably connect the receptacle to the base, including when the receptacle is in either the closed or open orientation. Moreover, the base includes an access opening, formed therein and extending there through, disposed in the aforementioned urine receiving relation to the mammal, con current to the operative position of the base on the animal/mammal. Cooperative structuring dimensioning and configuring between the connecting structure and the access opening serves to properly position or orient the receptacle, including the interior thereof, in the aforementioned urine receiving relation to the animal/mammal.

The structural and operative features of the connecting structure may vary and include one or more connecting members disposed, dimensioned and configured to pass through the access opening in removably connecting relation with the base such as, but not limited to, an interior surface of the base. As used and referred to herein, the interior surface of the base is that which is disposed in confronting relation to the under portion of the animal and is distinguishable from the exterior surface of the base, which is in an exposed position. As explained in greater detail hereinafter, the connecting structure, closure, access opening and receptacle interior may be accurately described as being in a substantially aligned relation to one another. Such an aligned relation facilitates their collective disposition in the urine receiving relation to the animal/mammal, concurrent to the base being in the aforementioned operative position.

As set forth herein, the urine collection device represented in this additional embodiment of the present invention may be structurally and operationally adapted for use with animals/mammals of different sizes, types, etc. Accordingly, additional features of the base include a retaining aperture formed therein and extending there through. The retaining aperture is disposed, dimensioned and configured to receive and retain a tale of the animal/mammal therein when the base is properly positioned in the operative position. Further, the access opening and the retaining aperture are disposed in an appropriately spaced distance from one another in different portions of the base. As such, the access opening and the retaining aperture may be respectively disposed in a leading half and a trailing half of the base, inwardly from an outer periphery of the base.

Therefore, the present invention in its various aspects provides an easy way of collecting urine from an animal/mammal with a possibility using the collected urine for diagnostic procedures.

The one or more embodiments of the urine collecting device of the present invention of the present invention is cost efficient to manufacture, easy to mount on the animal/mammal and poses a minimum of discomfort for the animal. Once urinating has finished the device is easily and quickly detached from the animal/mammal and the urine is conveniently collected in the receptacle from which it can easily be redistributed into analysis vials. Moreover, the device according to the present invention is suitable for use with mammals irrespective of the size, type and/or sex of the animal.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying drawings, at least one embodiment of the present invention is directed to a device for collecting urine from an animal/mammal, the device comprises: a base preferably in the form of a flexible sheet; wherein the flexible sheet is comprising a first surface to be facing the body of the mammal, and a second surface opposite to the first surface. The flexible sheet includes an extension in a lengthwise direction and an extension in a transverse direction, wherein the transverse direction is perpendicular to the lengthwise direction. The flexible sheet is at least partly made, from a moisture impervious material and at a specific location comprises a first trough-going hole in the flexible material sheet including a circumference.

The device further comprises a harness attached to the flexible sheet for allowing mounting of at least part of the flexible sheet below the pelvic region of the mammal. Further, the device comprises a receptacle for collecting urine from the mammal, which includes an inner surface and an outer surface. The inner surface is separated from the outer surface by a rim portion, wherein the receptable is being arranged in the first through-going hole at the rim portion thereof. As a result, the outer surface of the receptable extends away from the first through-going hole at the second or under surface of the flexible sheet.

Placing the harness around the back and rear part of the animal/mammal allows the mammal to carry the device while walking around. In this position, the receptable will be located at a lower point of the device which allows urine expelled from the animal to be collected in the receptable. Once urination has finished, the owner of the mammal or another person may secure the receptable and remove the device from the mammal.

In one embodiment of the device, a holding element is arranged in the first through-going hole at the circumference thereof. The holding element comprises a through-going-hole having an inner circumference, wherein the holding element is configured to be able to hold the receptable in the through-going hole thereof. Incorporation of the holding element in the first through-going hole of the sheet provides a beneficial way of allowing arrangement and connection of the receptable to the flexible sheet, via the through-going hole. Further, in one embodiment of the device of the present invention, the receptable and the holding element are configured for allowing removable mounting of the receptable in the through-going hole of the holding element. Providing removable mounting of the receptable in the through-going hole of the holding element provides easy distribution of the collected urine into vials suitable for analysis in that the receptable in this way can be removed from the rest of the device.

In one embodiment of the device of the present invention, the dimensions and configuration of the through-going hole of the holding element is adapted and/or substantially corresponds to the dimensions and configuration of the outer surface of the receptable in such a way that a tight seal may be established between an inner circumference of the through-going-hole of the holding element and the outer surface of the receptable. Further, the established tight seal may also be a releasable seal between the holding element and the receptable. Further, in one embodiment of the device of the present invention, the shape of the cross-section of the receptable is circular; rectangular, square; pentagonal; hexagonal; heptagonal; octagonal; nonagonal or decagonal. As such, the cross-section of the inner circumference of the through-going hole of the holding element may optionally correspond to the cross-sectional shape of the receptable. Such configurations of the type set forth herein will assure a tight seal between the holding element and the receptable.

In one embodiment of the device of the present invention, the flexible sheet base further comprises a second through-going hole for allowing the tail of the mammal to extend through the flexible sheet base via the second through-going hole. Therefore, the device will be suitable for use with animal/mammals even having a large tail.

Additional structural features in at least one embodiment of the device of the present invention comprise the flexible sheet being manufactured from a polymer, such as plastic, such as a thermoplastic polymer, such as polyethylene, polypropylene, PVC (polyvinyl chloride). Also, in the alternative, the flexible sheet may be manufactured from a cellulosic material, such as paper, such as paper being impregnated with a water impermeable impregnation; or any other material suitable for that purpose. Such materials are cost efficient, easy to handle and may be structured to provide secure a water tight barrier between two opposites surfaces of a sheet made from such materials.

In one embodiment of the device the present invention, the receptable is manufactured from a polymer, such as plastic, such as a thermoplastic polymer, such as polyethylene, polypropylene, PVC (polyvinyl chloride); or any other material suitable for that purpose. Such materials have proven suitable for the intended purpose. In cooperation there with one embodiment of the device includes the holding element being manufactured from a polymer, such as plastic, such as a thermoplastic polymer, such as polyethylene, polypropylene, PVC (Polyvinyl chloride); or any other material suitable for that purpose. Such materials have proven suitable for the intended purpose. Moreover, the holding element may be attached to the flexible sheet base by gluing, melting or by sliding. Such methods have proven suitable for fastening the holding element to the flexible sheet.

In one embodiment of the device of the present invention, the harness comprises 1, 2, 3 or 4 or more fasteners in the form of laces; and/or wherein the harness comprises 1, 2, 3 or 4 or more fasteners of the hook/loop type, such as Velcro® fasteners. The number and types of fasteners have proven efficient for fast mounting and release of the device on a mammal.

Additional structural and operative features also include the internal volume of the receptable being 50-700 ml, such as 100-600 ml, for example, 200-500 ml or 300-400 ml. These volumes are appropriate for most mammals being kept as pets. Also, the receptable may be made in whole or in part from a transparent and/or or translucent material. Providing the receptable of a transparent or translucent material allows one to easy and fast detect when urination has been finished.

Moreover, while the flexible sheet base may vary in size and configuration, dependent on the animal/mammal with which it is used, the device is configured to be adapted for use on a cat or a dog. Also, the flexible sheet independently may have an extension in the lengthwise direction of 50-85 cm, such as 55-80 cm, e.g. 60-75 cm or 65-70 cm; and/or wherein the flexible sheet independently is having an extension in the transverse direction of 35-60 cm, such as 40-55 cm or 50-55 cm. These dimensions are suitable for most mammals being kept as pets.

In one embodiment of the device of the present invention, the first through going hole is arranged in the middle third of the flexible sheet, measured in the transversal direction relative to the maximum extension of the sheet in the transversal direction. Moreover, the first through going hole is arranged in the most extreme third of the flexible sheet, measured in the longitudinal direction from one extreme end, relative to the maximum extension of the sheet in the longitudinal direction. Such position of the first through-going hole will assure a proper location of the receptable for receiving urine from the animal/mammal, once the device has been mounted on the mammal.

In cooperation there with, one embodiment of the device of the present invention, the second through going hole is arranged in the most extreme half of the flexible sheet, opposite to the location of the first through-going hole, and measured in the longitudinal direction, relative to the maximum extension of the sheet in the longitudinal direction. Such position of the second through-going hole will assure a proper location of the second through-going hole which will fit the location of the tail, once the device has been mounted on a mammal.

Additional aspects of the present invention relate to the use of a device as set forth above collecting urine from a mammal as well as the preparation of performing a diagnostic analysis of the mammal, based on the urine.

It should be understood that in the present description and in the appended claims, the use according to one aspect of the present invention does not include any diagnostic step(s) per se. The use thereof solely relates to the step of collecting urine from a mammal.

In yet another aspect, the present invention provides a method for collecting urine from a mammal, the method comprising the following steps:
i) providing a device according to the first aspect of the present invention;
ii) arranging the device on the mammal in such a way that the first surface of the flexible sheet is facing the mammal and in such a way that the receptable is located below the pelvic region of the mammal;
iii) strapping the harness around a back and/or rear portion of the mammal in order to secure the device to the mammal;
iv) awaiting the animal to start urinating;
v) once urinating has finished, unstrapping the device from the mammal and securing the urine.

Also, the method of this additional aspect of the present invention comprises the tail of the mammal, during step ii), is arranged so that it extends through the second through-going hole of the flexible sheet. Hereby any discomfort for the mammal is avoided.

Figure 1:
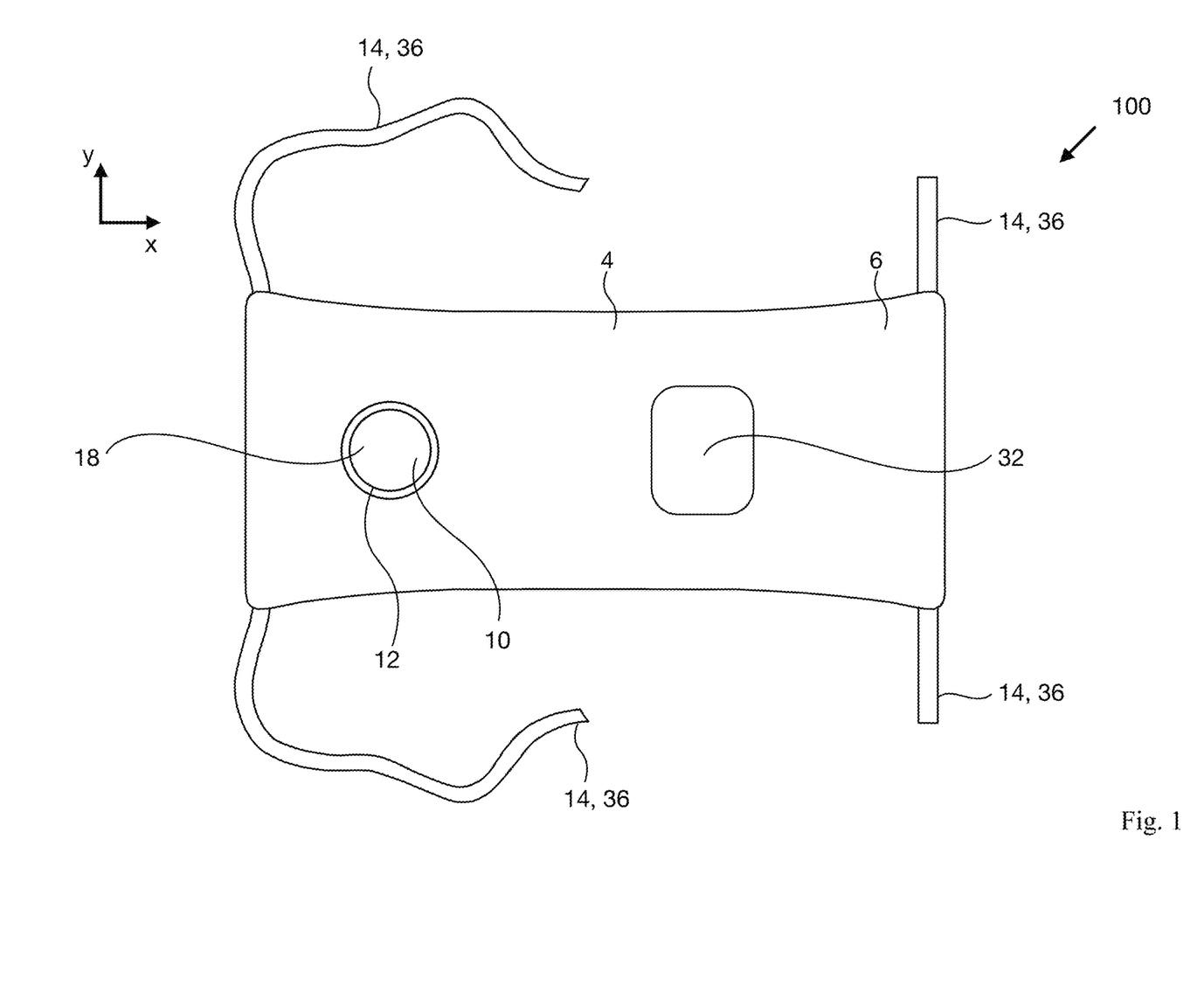
FIG. 1 is a plan view illustrating an embodiment of a device according to the first aspect of the present invention.
Figure 2:
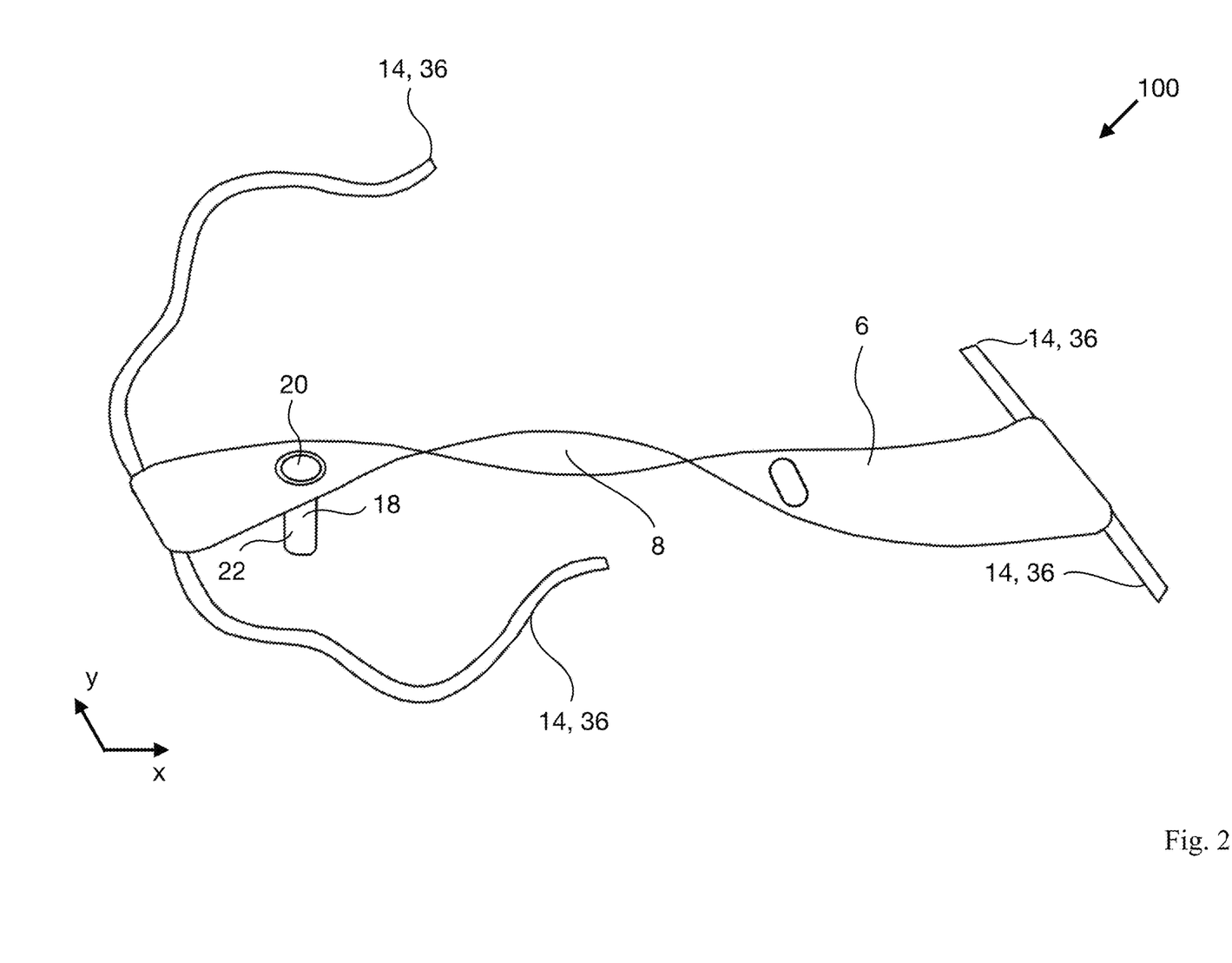
FIG. 2 is a perspective view illustrating an embodiment of a device according to the first aspect of the present invention.

Referring now to the figures for better illustrating the present invention, FIG. 1 and FIG. 2 are a plan view and a perspective view, respectively, illustrating an embodiment of a device according to the present invention.

Figure 5:
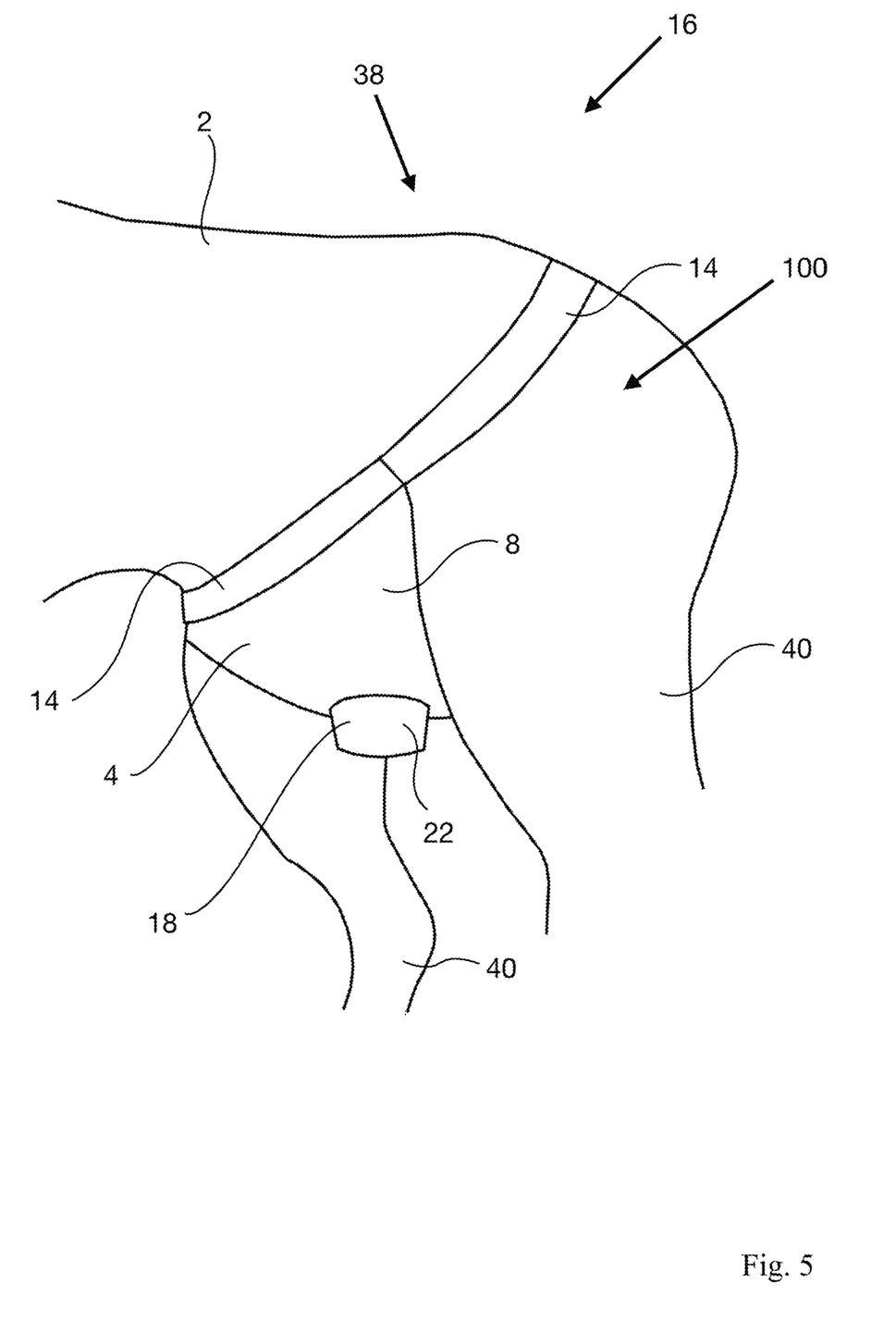
FIG. 5 is a perspective view illustrating a dog carrying a device according to the present invention as seen from a lower front position.
Figure 6:
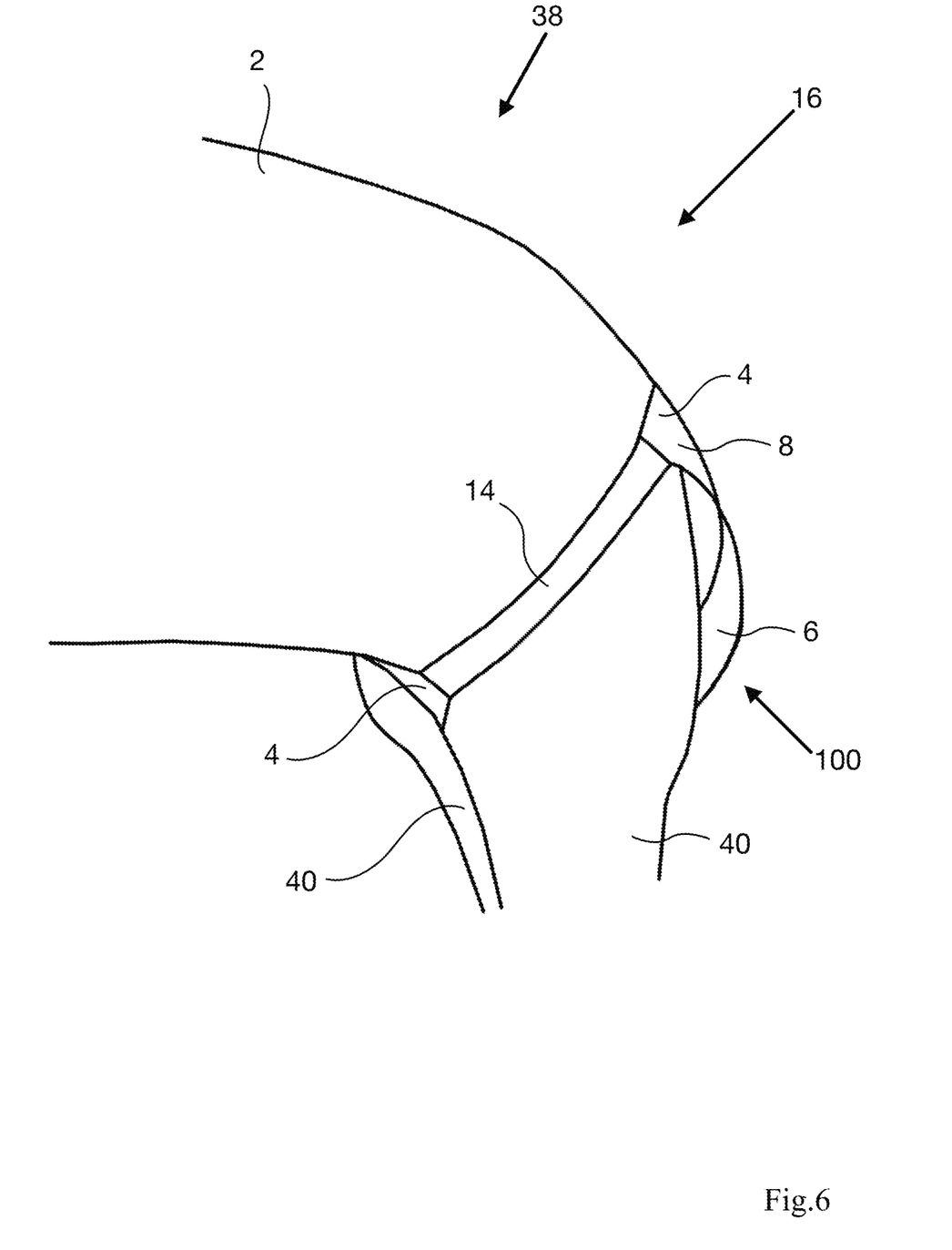
FIG. 6 is a perspective view illustrating a dog carrying a device according to the present invention as seen from the side of the dog.

FIG. 1 and FIG. 2 illustrate a device 100 for collecting urine from a mammal 2 (FIGS. 5 and 6). The device 100 comprises a flexible sheet 4 and a receptable 18 and a harness 14. The flexible sheet 4 comprises a first surface 6 intended to be facing the body of a mammal 2, and a second surface 8 opposite to the first surface. The flexible sheet 4 is extendable in a lengthwise direction X and also in a transversal direction Y, as illustrated schematically by the arrows, wherein the transversal direction is being perpendicular to the lengthwise direction.

The flexible sheet 4 is at least partly made, from a moisture impervious material and comprises, at a specific location, a first trough-going hole 10, thereby defining a circumference 12 of the hole 10. The harness 14 is attached to the flexible sheet 4 for mounting at least part of the flexible sheet 4 below the pelvic region 16 and exclusively between the legs of the mammal 2. Accordingly, this operative position serves to distinguish the device 100 from other known structures in the form of diapers or pants-like structures. A receptacle 18 for collecting urine from the mammal 2 is arranged in the flexible sheet 4. The receptable 18 comprises an inner surface 20 and an outer surface 22, wherein the inner surface 20 is separated from the outer surface 22 by a rim portion 24. In addition, the receptable 18 is being arranged in the first through-going hole 10 at the rim portion 24 thereof so that the outer surface 22 of the receptable extends outwardly and/or away from the first through-going hole 10 the second surface 8 of the flexible sheet 4.

In use, the device 100 is easily strapped around the pelvic region 16 of the mammal 2, as represented in FIGS. 5 and 6, exemplified by use with a dog 2. FIG. 5 shows that the device has been arranged on the dog 2 in such way that the first surface 6, opposite to the outer, second surface 8 of the flexible sheet 4 is facing the body of the dog in such a way that the receptable 18 is located below the pelvic region 16 of the dog. As also represented, the harness 14 of the device 100 has been strapped around a back and rear portion 38 of the dog in order to secure the device to the dog.

Once the device 100 is fixed to the dog 2, one awaits for the dog 2 to finish urinating. In the case where the receptable 18 is of a transparent or translucent material, it will be visibly evident when the receptable 18 has been loaded with urine. Subsequently, the device 100 is unstrapped from the dog 2 and the urine can be secured and relocated to analysis vials.

Figure 3:
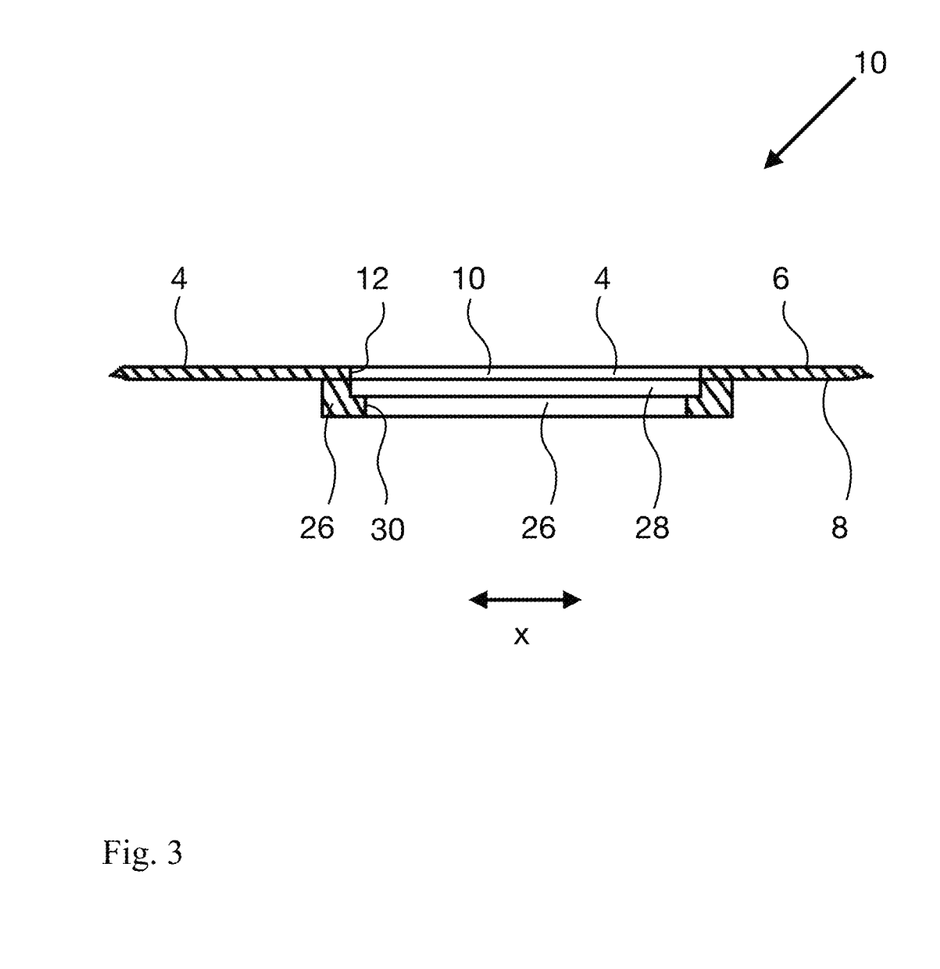
FIG. 3 is a cross-sectional view illustrating one embodiment of the design of holding element for the receptacle.

FIG. 3 is a cross-sectional view illustrating a one embodiment, wherein the first through-going hole 10 is formed in the flexible sheet 4. The cross-section illustrated in FIG. 3 is along a longitudinal line dividing the first through-going hole 10 in two parts of equal size. FIG. 3 shows the flexible sheet 4 having the first surface 6 and the second surface 8. In addition, the second surface 8 includes a holding element 26 for the receptable 18, which has been affixed to the flexible sheet 4 by gluing. The holding element 26 comprises a through-going hole 28 in its interior which is ring shaped. This through-going hole 28 itself comprises an inner circumference 30. The geometry and the dimensions of this inner circumference 30 is adapted to correspond to the configuration and the dimensions of the outer surface 22 of the receptable 18. Accordingly, the receptable 18 may be arranged in the through-going hole 28 of the holding element 26 and by exerting a mild pressing force, a tight seal will be established between the inner circumference 30 of the through-going hole 28 of the holding element 26 and the outer surface 22 of the receptable 18 on the other hand. Providing the through-going hole 10 of the flexible material with a holding element also allows for easy removal of the receptable 18 and thereby easy and safe relocation to the urine to diagnostic vials.

Figure 4:
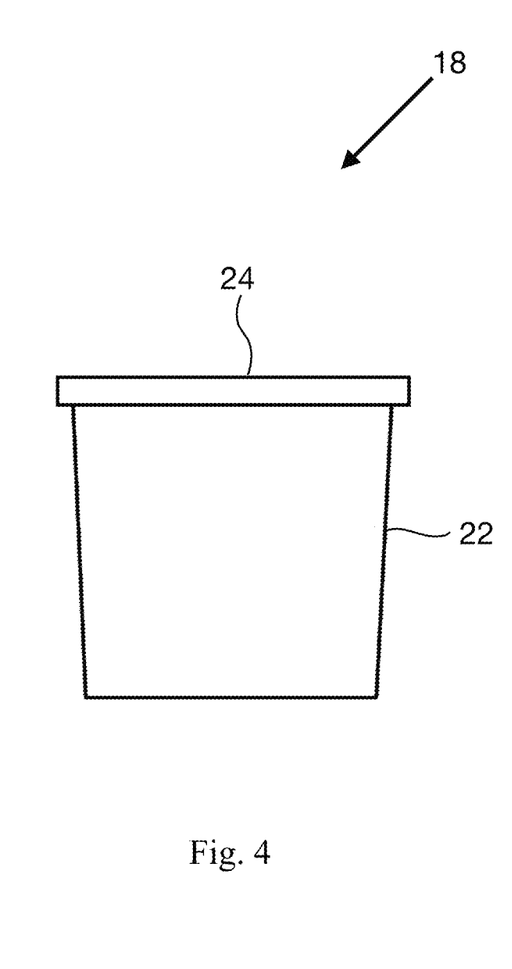
FIG. 4 is a side view illustrating a receptacle of the device according to the first aspect of the present invention.

FIG. 4 is a side view illustrating a receptable 18 of the device 100 and represents the receptable 18 having an inner surface 20 (not illustrated in FIG. 4) and an outer surface 22. The inner surface 20 and the outer surface 22 of the receptable 18 are separated by the rim portion 24. The rim portion 24 will prevent the receptable 18 from falling out of the through-going hole 28 in the holding element 26.

Yet another embodiment of the present invention is represented in the embodiments of FIGS. 7-14, wherein the urine collection device is generally indicated as 200. The device 200 may be considered operationally similar, but at least partially distinguishable in structure, from the urine collection device 100 as described above with primary reference to FIGS. 1-6.

More specifically, the urine collection device 200 includes a base 202 which is correspondingly and cooperatively dimensioned and configured for at least partially covering relation to an animal/mammal 2, as represented in FIGS. 5 and 6, on which it is mounted. As such, the base 202 may include a flexible and possibly "stretchable" material sheet 204 dimensioned and configured to accommodate animals which may differ in size, type and sex.

In addition, a harness 206 is connected to the base 202 and serves to removably connect it in an operative position on the animal/mammal 2. For purposes of clarity, the "operative position" may be similar to that represented in FIGS. 5 and 6 and may be more specifically defined as being positioned in a manner which facilitates the collection of urine from the mammal 2, in the manner set forth in greater detail hereinafter. Therefore, when in the operative position, the base 202 is disposed in overlying, covering relation to an under portion of the animal/mammal, such as generally beneath the pelvic area 16 as represented in FIGS. 5 and 6. Also, the operative position of the base 202 and flexible sheet 204 may be disposed exclusively between the legs of the animal 2, thereby distinguishing the operative position from diaper or pant-like structures, in which the legs of the animal are at least partially enclosed.

Accordingly, the harness 206 may include one or more straps 208, 208' or other appropriately structured members attached to the base 202 and disposed in interconnecting relation to one another and/or to the base 202. Further, the harness 206 may include one or more attachment members 210 which may be appropriately positioned on the straps 208 and 208' as well as on the base 202 and sheet 204, as represented in at least FIGS. 7, 8 and 10. When so positioned, the attachment members 210 may be interconnected to one another, when the base 202 is disposed on the animal 2 in the operative position. The attachment members 210 may be hook and loop type fasteners commercially known as the Velcro® fasteners or other type attachment structures which facilitate the removable attachment of the harness 206 and the base 202 in the operative position.

Figure 14:
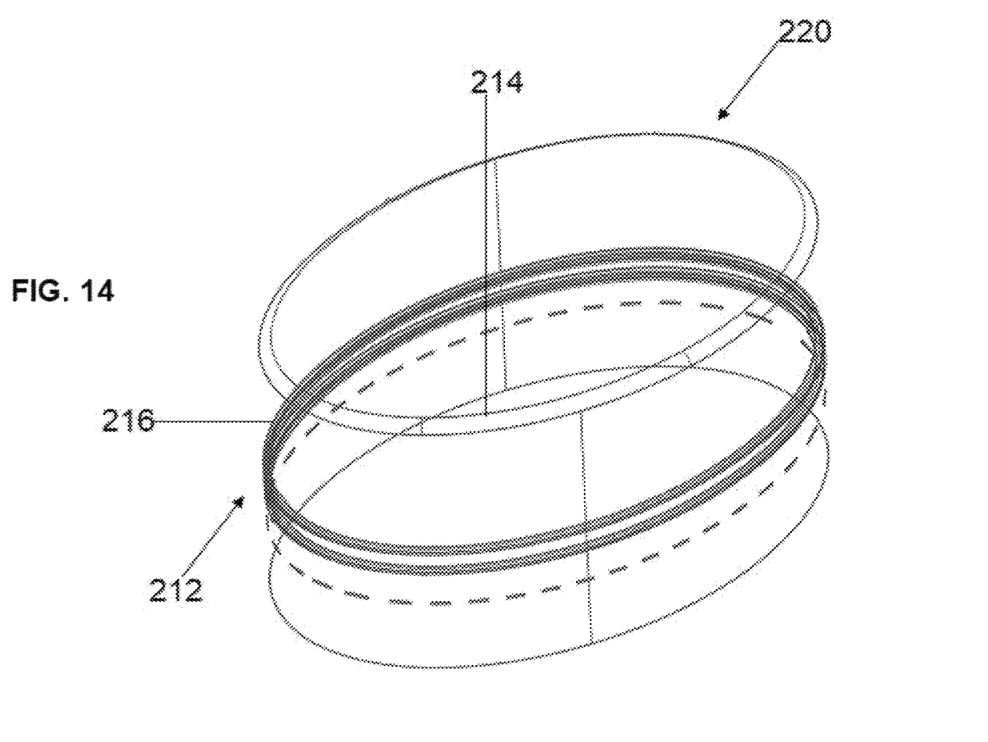
FIG. 14 is a perspective view of the receptacle of the embodiment of FIGS. 11-13 in an open orientation.

Additional features of the urine collection device 200 of the present invention includes a receptacle 212 having a hollow interior 214, as represented in at least FIG. 14. The hollow interior 214 is appropriately dimensioned to receive urine passed from the animal/mammal 2. The dimension of the hollow interior 214 may be substantially equivalent to that described in detail herein with reference to the embodiment of FIGS. 1-6. As represented throughout the Figures, the receptacle 212 is connected to the base 202 in urine receiving relation to the mammal 2, similar to the embodiment of FIGS. 5 and 6, concurrent to the base 202 being mounted in the aforementioned operative position.

Figure 11:
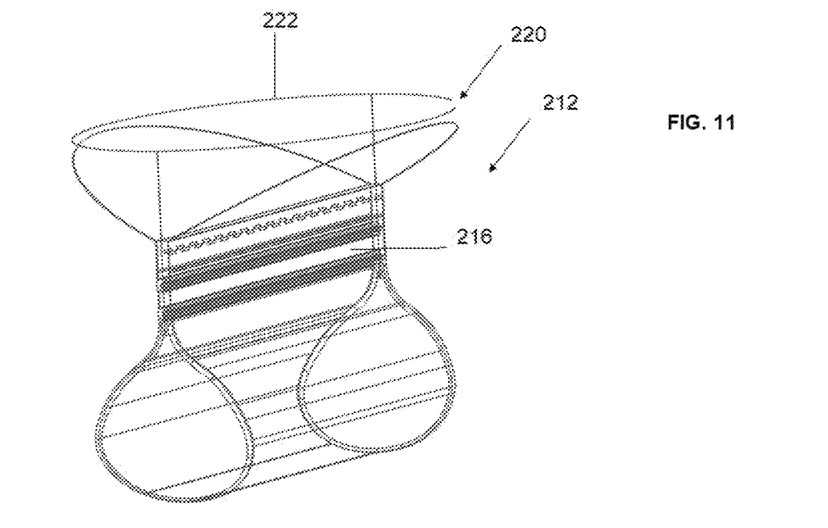
FIG. 11 is a perspective view of a receptacle component of the embodiment of FIG. 7-10 in a closed orientation.
Figure 12:
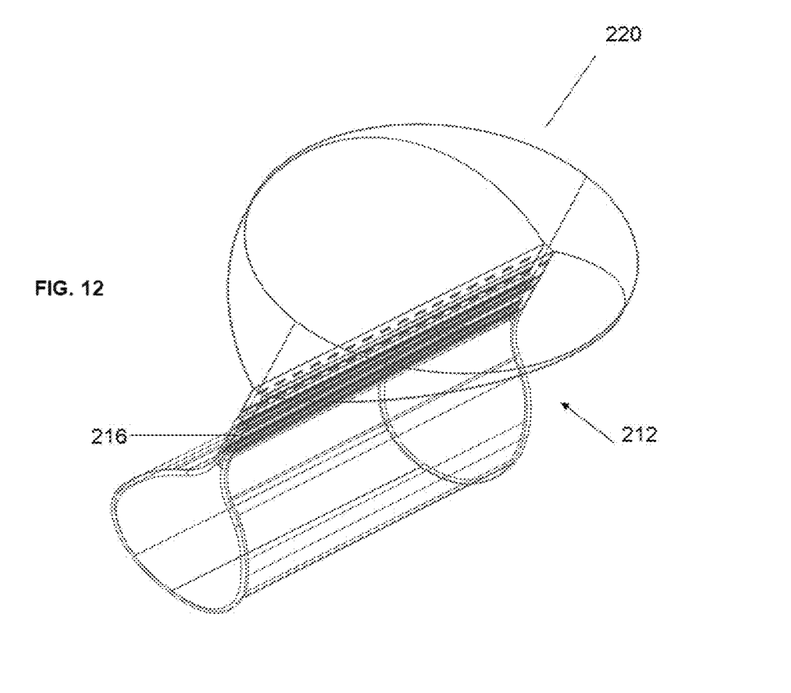
FIG. 12 is a perspective view of the embodiment of FIG. 11.
Figure 13:
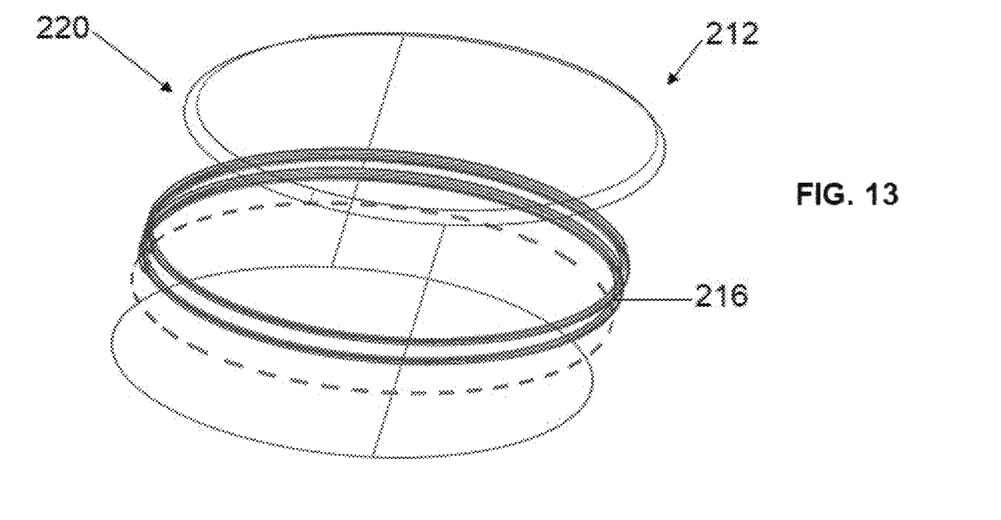
FIG. 13 is a perspective view of the receptacle of the embodiment of FIGS. 11 and 12 in an open orientation.

As represented in detail in FIGS. 11-14, the receptacle 212 preferably includes a closure 216 structured for disposition in a closed orientation, as represented in FIGS. 11, 12 and an open orientation as represented in FIGS. 13 and 14, relative to the hollow interior 214. As represented in FIGS. 11, 12 and FIGS. 13, 14, the closure 216 is cooperatively structured with the base 202, such that the closure 216 may be selectively disposed in either of the closed or open orientations, concurrent to it being connected to the base 202, while the base 202 is disposed in the operative position on the animal/mammal 2. Additional structural features of the closure 216 facilitate it defining a substantially fluid tight seal, when in the closed orientation, thereby preventing or significantly restricting leakage of the collected urine from the interior 214 of the receptacle 212.

The embodiment of the urine collection device 200 also includes a connecting structure 220 attached to the receptacle 212 and structured to removably connect the receptacle 212 to the flexible sheet 204 of the base 202. As represented in FIGS. 7, 8 and FIGS. 9, 10, the connecting structure 220 is structurally operative to connect the receptacle 212 to the base 202, when the receptacle 212 is in either the closed or open orientation.

As also represented throughout the Figures, removable interconnection of the receptacle 212 is preferably accomplished by the provision of an access opening 230 being cooperatively structured, dimensioned and configured with the connecting structure 220. More specifically, the flexible sheet 204 of the base 202 includes an access opening 230, formed therein and extending there through. The access opening 230 is disposed in the aforementioned urine receiving relation to the mammal 2, concurrent to the operative position of the base 202 on the animal/mammal 2. Cooperative structuring, dimensioning and configuring between the connecting structure 216 and the access opening 230 serves to properly position, orient and/or align the receptacle 202, including the interior 214 thereof, in the aforementioned urine receiving relation to the animal/mammal 2.

The structural and operative features of the connecting structure 220 may vary and include at least one and/or one or more connecting members 222 disposed, dimensioned and configured to pass through the access opening 230, or otherwise be disposed in direct fluid communication there with, and thereby serve to removably connect the receptacle 212 to the base 202. Such removable interconnection of the connecting structure 220 and/or one or more connecting members 222 may comprise, but not limited to, the one or more connecting members 222 engaging, being attached to and/or confronting an interior surface 205 and/or an exterior surface 207 of the flexible sheet 204 base 202, as represented in at least FIGS. 7 and 8. As used and referred to herein, the interior surface 205 of the base 202 is that which is disposed in confronting relation to the under portion of the animal 2 and is distinguishable from the exterior surface 207 (see FIG. 9) of the base 202, which is in an exposed position, relative to an exterior of the base 202.

Figure 7:
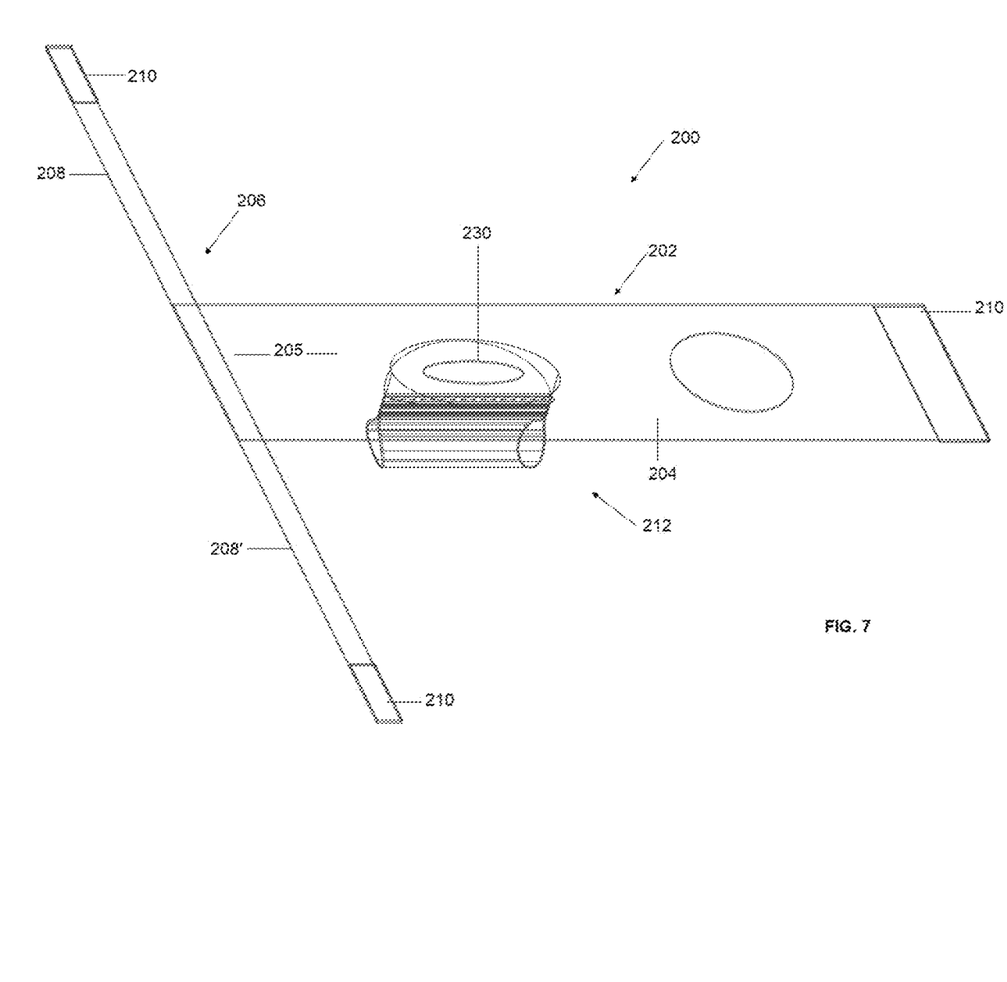
FIG. 7 is a perspective view of another embodiment of the urine collecting device of the present invention in an assembled state.
Figure 8:
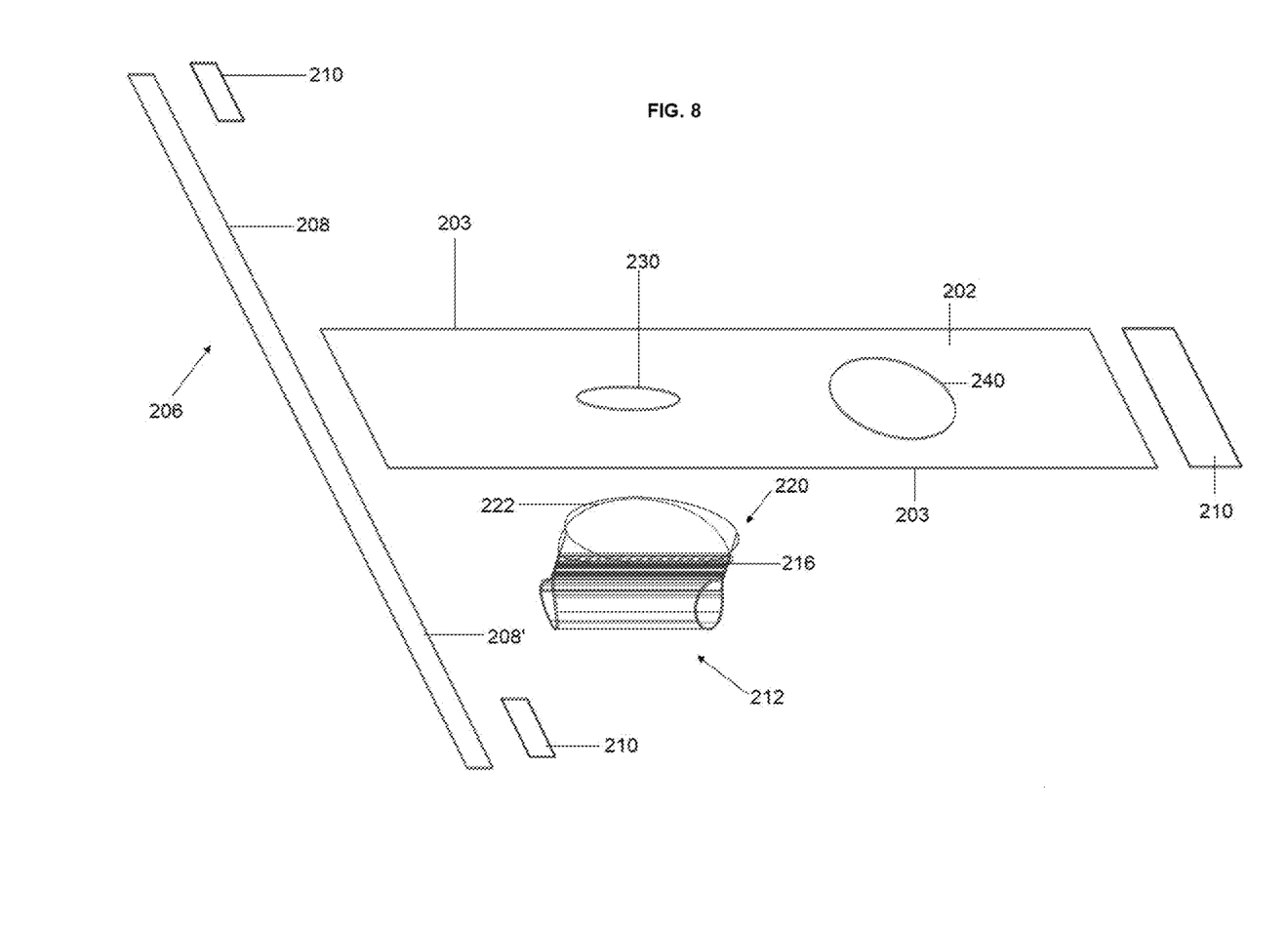
FIG. 8 is a perspective view in exploded form of the embodiment of FIG. 7 in an unassembled state.
Figure 9:
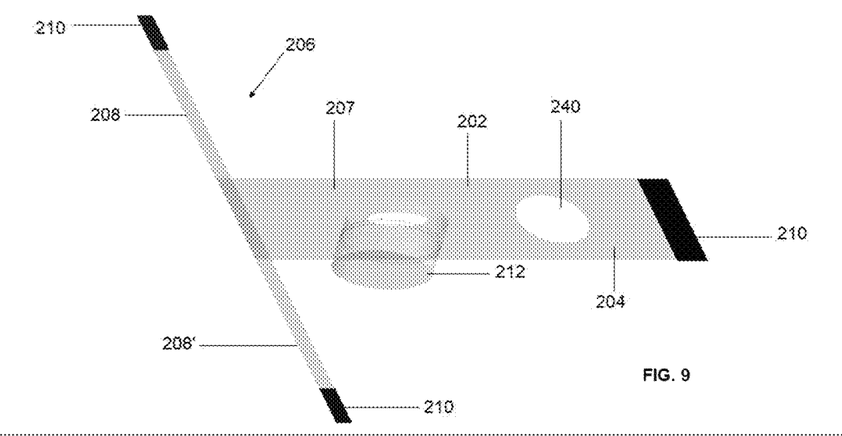
FIG. 9 is a perspective view of the embodiment of FIGS. 7 and 8 in an assembled form.
Figure 10:
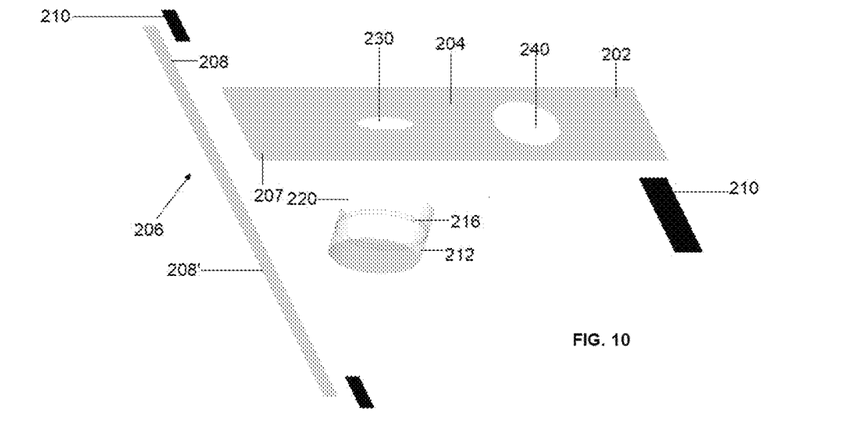
FIG. 10 is a perspective view in exploded form of the embodiment of FIGS. 7-9 in an unassembled state.

As represented throughout the Figures, the connecting structure 220, closure 216, access opening 230 and the interior 214 of the receptacle 212 may be accurately described as being in a substantially aligned relation to one another (See FIGS. 7 and 9). Such an aligned relation facilitates their collective disposition in the urine receiving relation to the animal/mammal 2, concurrent to the base 202 being in the aforementioned operative position on the animal/mammal 2.

As set forth herein, the urine collection device 200 represented in this additional embodiment of the present invention may be structurally and operationally adapted for use with animals/mammals of different sizes, types, etc. Accordingly, additional features of the base 202 include a retaining aperture 240 formed in the flexible sheet 204 and extending there through. The retaining aperture 240 2 is disposed, dimensioned and configured to receive and retain a tale of the animal/mammal 2 therein when the base 202 is properly positioned on the animal/mammal 2 in the operative position. Further, the access opening 230 and the retaining aperture 240 are disposed in an appropriately spaced distance from one another, in different portions of the base 202. As such, the access opening 230 and the retaining aperture 240 may be respectively disposed in a leading half and a trailing half of the base 202, inwardly from an outer periphery 203 of the base 202.

It should be understood that all features discussed above and in the appended claims in relation to the present invention and embodiments thereof may apply equally well to the other embodiments of the present invention.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A device for collecting urine from a mammal, said device comprising:
    a base correspondingly dimensioned and configured for at least partial covering of the mammal,
    a harness connected to said base and structured to removably secure said base to the mammal in an operative position,
    a receptacle, including a hollow interior, connected to said base in urine receiving relation to the mammal, concurrent to said operative position, and
    said receptacle including a closure structured for disposition in a closed orientation and an open orientation relative to said hollow interior, concurrent to said connection of said receptacle to said base.

2. The device as recited in 1 wherein said closure is integrally attached to said receptacle.

3. The device as recited in claim 2 wherein said closure is structured to define a fluid seal between said hollow interior and an exterior of said closure.

4. The device as recited in claim 1 further comprising a connecting structure attached to said receptacle and structured to removably connect said receptacle to said base.

5. The device as recited in claim 4 further comprising an access opening formed in said base in said urine receiving relation to the mammal, concurrent to said operative position.

6. The device as recited in claim 5 wherein said receptacle is connected to said base in fluid communicating relation between said access opening and said hollow interior of said receptacle.

7. The device as recited in claim 5 wherein said connecting structure is dimensioned and configured to at least partially pass through said access opening to define said removable connection of said receptacle to said base.

8. The device as recited in claim 5 wherein said connecting structure includes at least one connecting member attached to said receptacle exteriorly of said closure, said at least one connecting member disposed within said access opening in removably attached relation to an interior surface of said base.

9. The device as recited in claim 1 wherein said base comprises a flexible material sheet dimensioned and configured to extend exclusively between the mammals rear legs, in covering relation to under portions of a pelvic area of the mammal, concurrent to said operative position.

10. The device as recited in claim 9 wherein said sheet is at least partially formed of a liquid impermeable material.

11. The device as recited in claim 1 wherein said base includes a retaining aperture disposed and structured to receive and retain a tale of the mammal therein, concurrent to said operative position.

12. The device as recited in claim 11 further comprising an access opening formed in said base in urine receiving relation to the mammal, concurrent to said operative position.

13. A device for collecting urine from a mammal, said device comprising:
    a base formed of a flexible material dimensioned and configured to overlie at least an under portion of the mammal,
    a harness connected to said base and structured to removably secure said base to the mammal in an operative position,
    an access opening formed in said base in urine receiving relation to the mammal, concurrent to said operative position,
    a receptacle, including an integrally connected closure, removably connected to said base, in said urine receiving relation, via said access opening, and
    said closure disposable between an open orientation and a closed orientation.

14. The device as recited in claim 13 wherein said closure is structured for disposition between said open orientation and said closed orientation, concurrent to connection to said base in said operative position.

15. The device as recited in claim 13 wherein said base includes a retaining aperture disposed and structured to receive and retain a tale of the mammal therein, concurrent to said operative position.

16. The device as recited in claim 15 wherein said access opening and said retaining aperture are respectively disposed in a leading half and a trailing half of said base, in spaced relation to one another and inwardly from a periphery of said base.

17. The device as recited in claim 13 wherein said base is dimensioned and cooperatively structured with said harness to extend exclusively between the mammals rear legs, concurrent to said operative orientation.

18. The device as recited in claim 13 further comprising a connecting structure mounted on said receptacle and disposed in removable interconnecting relation between said base and said receptacle, via said access opening, concurrent to said operative position.

19. The device as recited in claim 18 wherein said connecting structure is dimensioned and configured to at least partially pass through said access opening to define said removable connection of said receptacle to said base.

20. The device as recited in claim 19 wherein said connecting structure includes a plurality of connecting members attached to said receptacle exteriorly of said closure, said plurality of connecting structures disposed through said access opening in removably attached relation to said base.

* * * * *